(12) United States Patent
Wilcox et al.

(10) Patent No.: US 8,277,426 B2
(45) Date of Patent: Oct. 2, 2012

(54) MALE URINARY INCONTINENCE DEVICE

(76) Inventors: Heather J. Wilcox, Columbus, OH (US); Nolan M. Wilcox, Columbus, OH (US)

( * ) Notice: Subject to any disclaimer, the term of this patent is extended or adjusted under 35 U.S.C. 154(b) by 416 days.

(21) Appl. No.: 12/570,188

(22) Filed: Sep. 30, 2009

(65) Prior Publication Data

US 2011/0077606 A1    Mar. 31, 2011

(51) Int. Cl.
    *A61F 13/471*      (2006.01)
    *A41D 13/05*      (2006.01)
(52) U.S. Cl. ............... 604/349; 604/365.101; 2/466
(58) Field of Classification Search ............ 604/385.09, 604/349, 378, 385.19; 2/466
See application file for complete search history.

(56) References Cited

U.S. PATENT DOCUMENTS

| | | |
|---|---|---|
| 3,220,409 A | 11/1965 | Liloia et al. |
| 3,532,093 A * | 10/1970 | Lovret ............... 604/348 |
| 3,613,123 A * | 10/1971 | Langstrom ............ 4/144.3 |
| 3,782,375 A * | 1/1974 | Donars .................. 602/72 |
| 3,926,891 A | 12/1975 | Gross et al. |
| 3,958,574 A | 5/1976 | Rohr |
| 3,999,550 A | 12/1976 | Martin |
| 4,190,562 A | 2/1980 | Westerman |
| 4,239,044 A | 12/1980 | Pavlinch |
| 4,284,079 A | 8/1981 | Adair |
| 4,293,609 A | 10/1981 | Erickson |
| 4,324,246 A | 4/1982 | Mullane et al. |
| 4,342,314 A | 8/1982 | Radel et al. |
| 4,384,577 A | 5/1983 | Huber et al. |
| 4,393,080 A | 7/1983 | Pawelchak et al. |
| D271,800 S | 12/1983 | Brendling |
| 4,453,938 A * | 6/1984 | Brendling ............ 604/346 |
| 4,477,325 A | 10/1984 | Osburn |
| 4,522,624 A | 6/1985 | Bolick |
| 4,534,767 A | 8/1985 | Habib |
| 4,549,530 A | 10/1985 | Finney |
| 4,551,490 A | 11/1985 | Doyle et al. |
| 4,559,051 A | 12/1985 | Hanson |
| 4,571,749 A | 2/1986 | Fischell |
| 4,589,875 A | 5/1986 | Stringer |
| 4,589,877 A | 5/1986 | Sivilich |

(Continued)

FOREIGN PATENT DOCUMENTS

EP      57057 A1      8/1982

(Continued)

OTHER PUBLICATIONS

Gennari, Silvia, International Search Report and Written Opinion of the International Searching Authority, Feb. 10, 2011.

(Continued)

*Primary Examiner* — Melanie Hand
*Assistant Examiner* — Paula Craig
(74) *Attorney, Agent, or Firm* — The Richards Law Firm LLC; William B. Richards, Esq.

(57) ABSTRACT

A male urinary incontinence device is provided which includes a body, the body having a shell, and the shell forming a cavity adapted to hold male genitalia. An absorbent, suitable for absorbing urine, is at least partially disposed within the cavity and a moisture barrier is positioned adjacent the body to help protect clothing from urine soiling. A liquid-permeable liner is attached to the body in a spaced-apart relation to the absorbent. To create a hammock-like effect, the liquid-permeable liner may be attached at the perimeter of the body.

19 Claims, 4 Drawing Sheets

U.S. PATENT DOCUMENTS

| | | | |
|---|---|---|---|
| 4,627,846 A * | 12/1986 | Ternstrom | 604/349 |
| 4,673,401 A | 6/1987 | Jensen et al. | |
| 4,675,012 A | 6/1987 | Rooyakkers | |
| 4,676,785 A * | 6/1987 | Battista | 604/369 |
| 4,681,577 A * | 7/1987 | Stern et al. | 604/378 |
| 4,695,279 A | 9/1987 | Steer | |
| 4,731,083 A | 3/1988 | Fischell | |
| 4,768,503 A | 9/1988 | Highgate et al. | |
| 4,769,020 A | 9/1988 | Eaton | |
| 4,770,445 A | 9/1988 | Steer et al. | |
| 4,772,280 A | 9/1988 | Rooyakkers | |
| 4,784,660 A | 11/1988 | Fischell | |
| 4,800,900 A | 1/1989 | French | |
| 4,804,380 A | 2/1989 | Lassen et al. | |
| 4,813,943 A * | 3/1989 | Smith | 604/329 |
| 4,820,289 A | 4/1989 | Coury et al. | |
| 4,855,335 A | 8/1989 | Neperud | |
| 4,880,016 A | 11/1989 | Worth et al. | |
| 4,885,049 A | 12/1989 | Johannesson | |
| 4,892,536 A * | 1/1990 | DesMarais et al. | 604/385.27 |
| 4,909,243 A | 3/1990 | Frank et al. | |
| 4,942,886 A | 7/1990 | Timmons | |
| 4,950,264 A | 8/1990 | Osborn, III | |
| 4,990,147 A * | 2/1991 | Freeland | 604/385.22 |
| 5,004,463 A | 4/1991 | Nigay | |
| 5,009,649 A | 4/1991 | Goulter et al. | |
| 5,009,653 A | 4/1991 | Osborn, III | |
| 5,036,839 A | 8/1991 | Weiss et al. | |
| 5,041,092 A | 8/1991 | Barwick | |
| 5,074,853 A | 12/1991 | Bryant | |
| 5,075,344 A | 12/1991 | Johnson | |
| 5,084,037 A | 1/1992 | Barnett | |
| 5,112,324 A | 5/1992 | Wallace | |
| 5,163,897 A | 11/1992 | Persky | |
| 5,171,236 A * | 12/1992 | Dreier et al. | 604/369 |
| 5,211,640 A | 5/1993 | Wendler | |
| 5,269,775 A * | 12/1993 | Freeland et al. | 604/385.22 |
| 5,275,592 A * | 1/1994 | Grizzaffi | 604/396 |
| 5,300,052 A * | 4/1994 | Kubo | 604/349 |
| 5,306,266 A * | 4/1994 | Freeland | 604/385.19 |
| 5,342,332 A | 8/1994 | Wheeler | |
| 5,344,516 A * | 9/1994 | Tanji et al. | 156/164 |
| 5,366,451 A * | 11/1994 | Levesque | 604/378 |
| 5,380,310 A | 1/1995 | Mitrani | |
| 5,380,312 A | 1/1995 | Goulter | |
| 5,401,266 A | 3/1995 | Runeman et al. | |
| 5,409,474 A | 4/1995 | Fleeman-Hardwick | |
| 5,409,475 A | 4/1995 | Steer | |
| 5,415,179 A | 5/1995 | Mendoza | |
| 5,429,622 A * | 7/1995 | Chung | 604/312 |
| 5,486,168 A | 1/1996 | Runeman et al. | |
| 5,495,858 A | 3/1996 | Steer et al. | |
| 5,500,270 A * | 3/1996 | Langdon et al. | 428/119 |
| 5,520,606 A | 5/1996 | Schoolman et al. | |
| 5,520,875 A | 5/1996 | Wnuk et al. | |
| 5,527,300 A * | 6/1996 | Sauer | 604/378 |
| 5,531,725 A | 7/1996 | Steer | |
| 5,545,155 A * | 8/1996 | Hseih et al. | 604/378 |
| 5,554,149 A | 9/1996 | O'Donnell | |
| 5,556,393 A | 9/1996 | Ronnberg | |
| 5,558,659 A * | 9/1996 | Sherrod et al. | 604/385.26 |
| 5,558,734 A * | 9/1996 | Sherrod et al. | 156/164 |
| 5,569,231 A | 10/1996 | Emenaker et al. | |
| 5,571,118 A | 11/1996 | Boutos | |
| 5,571,125 A | 11/1996 | Chadwick | |
| 5,603,946 A | 2/1997 | Constantine | |
| 5,607,415 A | 3/1997 | Datta et al. | |
| 5,618,277 A | 4/1997 | Goulter | |
| 5,618,279 A | 4/1997 | Pudlo | |
| 5,624,421 A * | 4/1997 | Dabi et al. | 604/378 |
| 5,630,429 A | 5/1997 | Dann | |
| D380,547 S | 7/1997 | Carlsen | |
| 5,643,235 A | 7/1997 | Figuerido | |
| 5,651,778 A | 7/1997 | Melius et al. | |
| 5,665,186 A | 9/1997 | Datta et al. | |
| 5,669,893 A | 9/1997 | Tanghøj | |
| 5,676,688 A | 10/1997 | Jaker et al. | |
| 5,685,870 A | 11/1997 | Tanghøj | |
| 5,695,376 A * | 12/1997 | Datta et al. | 442/334 |
| 5,695,485 A | 12/1997 | Duperret et al. | |
| 5,702,381 A | 12/1997 | Cottenden | |
| 5,704,893 A | 1/1998 | Timm | |
| 5,705,249 A | 1/1998 | Takai et al. | |
| 5,716,350 A | 2/1998 | Ryan | |
| 5,727,568 A | 3/1998 | Kiser | |
| 5,735,837 A | 4/1998 | Ishikawa | |
| 5,752,944 A | 5/1998 | Dann et al. | |
| 5,792,132 A * | 8/1998 | Garcia | 604/385.01 |
| 5,797,890 A | 8/1998 | Goulter et al. | |
| 5,817,086 A * | 10/1998 | Kling | 604/385.19 |
| 5,827,257 A * | 10/1998 | Fujioka et al. | 604/385.19 |
| 5,827,259 A * | 10/1998 | Laux et al. | 604/385.29 |
| 5,842,968 A | 12/1998 | Johnson | |
| 5,873,868 A * | 2/1999 | Nakahata | 604/383 |
| 5,882,769 A | 3/1999 | McCormack et al. | |
| 5,884,629 A | 3/1999 | O'Brien | |
| 5,885,264 A * | 3/1999 | Matsushita | 604/361 |
| D412,031 S | 7/1999 | Oscarsson | |
| 5,941,863 A * | 8/1999 | Guidotti et al. | 604/378 |
| 5,947,947 A * | 9/1999 | Tanzer et al. | 604/385.101 |
| 6,010,001 A | 1/2000 | Osborn, III | |
| 6,010,489 A | 1/2000 | Blackburn | |
| 6,011,194 A | 1/2000 | Buglino et al. | |
| 6,059,762 A | 5/2000 | Boyer et al. | |
| 6,074,341 A | 6/2000 | Anderson et al. | |
| 6,105,174 A | 8/2000 | Nygren et al. | |
| 6,119,697 A | 9/2000 | Engel et al. | |
| D432,233 S | 10/2000 | Stasi et al. | |
| 6,131,576 A | 10/2000 | Davis | |
| 6,131,736 A | 10/2000 | Farris et al. | |
| 6,132,409 A * | 10/2000 | Vogt et al. | 604/348 |
| 6,138,678 A | 10/2000 | Nilsson | |
| D434,144 S | 11/2000 | Anderson | |
| 6,143,798 A | 11/2000 | Jensen et al. | |
| 6,167,886 B1 | 1/2001 | Engel et al. | |
| 6,197,011 B1 | 3/2001 | Freitas et al. | |
| 6,203,512 B1 | 3/2001 | Farris et al. | |
| 6,209,142 B1 | 4/2001 | Mattsson | |
| 6,293,923 B1 | 9/2001 | Yachia et al. | |
| 6,299,607 B1 | 10/2001 | Osborn, III et al. | |
| 6,315,765 B1 * | 11/2001 | Datta et al. | 604/385.24 |
| 6,349,727 B1 | 2/2002 | Stewart, Jr. | |
| 6,382,214 B1 | 5/2002 | Raz et al. | |
| 6,384,297 B1 | 5/2002 | Colman et al. | |
| 6,387,041 B1 | 5/2002 | Harari et al. | |
| 6,398,718 B1 | 6/2002 | Yachia et al. | |
| 6,406,462 B1 | 6/2002 | Johnson | |
| 6,416,500 B1 * | 7/2002 | Wada et al. | 604/349 |
| 6,419,665 B1 | 7/2002 | Cohen | |
| 6,443,930 B1 | 9/2002 | Silverstein | |
| 6,447,493 B1 | 9/2002 | Simpson et al. | |
| 6,463,932 B1 | 10/2002 | Single et al. | |
| 6,478,763 B1 | 11/2002 | Simonsen et al. | |
| 6,502,578 B2 | 1/2003 | Raz et al. | |
| 6,508,794 B1 * | 1/2003 | Palumbo et al. | 604/317 |
| 6,530,909 B1 * | 3/2003 | Nozaki et al. | 604/349 |
| D473,303 S | 4/2003 | Harriz et al. | |
| D473,304 S | 4/2003 | Harriz et al. | |
| 6,544,273 B1 | 4/2003 | Harari et al. | |
| 6,565,545 B1 | 5/2003 | Frenche | |
| 6,569,135 B1 | 5/2003 | Mula | |
| 6,602,234 B2 * | 8/2003 | Klemp et al. | 604/385.01 |
| 6,612,977 B2 | 9/2003 | Staskin et al. | |
| 6,613,027 B2 | 9/2003 | Kulikov | |
| 6,613,954 B1 | 9/2003 | Horney et al. | |
| 6,617,490 B1 | 9/2003 | Chen et al. | |
| 6,632,204 B2 | 10/2003 | Guldfeldt et al. | |
| 6,635,037 B1 | 10/2003 | Bennett | |
| 6,635,038 B2 | 10/2003 | Scovel | |
| 6,652,450 B2 | 11/2003 | Neisz et al. | |
| 6,652,499 B1 | 11/2003 | Edgren et al. | |
| 6,659,936 B1 | 12/2003 | Furness et al. | |
| 6,679,867 B2 | 1/2004 | Miskie | |
| 6,682,511 B2 | 1/2004 | Besoyan | |
| 6,691,711 B2 | 2/2004 | Raz et al. | |
| 6,692,603 B1 | 2/2004 | Lindsay et al. | |
| 6,702,798 B2 | 3/2004 | Christoffel et al. | |

| | | |
|---|---|---|
| 6,723,078 B1 | 4/2004 | Pennington et al. |
| 6,730,110 B1 | 5/2004 | Harari et al. |
| 6,746,421 B2 | 6/2004 | Yachia et al. |
| 6,802,807 B2 | 10/2004 | Anderson et al. |
| 6,805,662 B2 | 10/2004 | Shah et al. |
| 6,817,992 B1 | 11/2004 | Sassak et al. |
| 6,827,085 B2 | 12/2004 | Single et al. |
| 6,843,253 B2 | 1/2005 | Parkes |
| 6,911,003 B2 | 6/2005 | Anderson |
| 6,960,218 B2 | 11/2005 | Rennich |
| 6,964,643 B2 | 11/2005 | Hovland et al. |
| 6,971,986 B2 | 12/2005 | Staskin et al. |
| 6,979,325 B2 | 12/2005 | Reddy |
| 6,981,505 B2 | 1/2006 | Krause et al. |
| 7,000,260 B2 | 2/2006 | Rajala et al. |
| 7,014,635 B2 | 3/2006 | Goulter |
| 7,015,370 B2 * | 3/2006 | Watanabe et al. ............ 604/378 |
| 7,048,682 B2 | 5/2006 | Neisz et al. |
| 7,066,920 B1 | 6/2006 | Mula |
| 7,083,568 B2 | 8/2006 | Neisz et al. |
| 7,104,976 B1 | 9/2006 | Allen, Sr. |
| 7,107,995 B2 | 9/2006 | Parkes |
| RE39,371 E | 10/2006 | Johnson |
| 7,125,399 B2 | 10/2006 | Miskie |
| 7,137,971 B2 | 11/2006 | Tanzer |
| 7,143,768 B2 | 12/2006 | Miskie |
| 7,147,606 B1 | 12/2006 | Chang et al. |
| 7,160,276 B2 | 1/2007 | Bruns |
| 7,160,277 B2 | 1/2007 | Elson et al. |
| 7,163,528 B2 | 1/2007 | Christon et al. |
| 7,166,092 B2 | 1/2007 | Elson et al. |
| 7,175,613 B2 * | 2/2007 | Sugiyama et al. ....... 604/385.14 |
| 7,185,761 B2 | 3/2007 | Molina et al. |
| 7,198,597 B2 | 4/2007 | Siegel et al. |
| 7,217,259 B2 | 5/2007 | McDaniel |
| 7,226,408 B2 | 6/2007 | Harai et al. |
| 7,229,453 B2 | 6/2007 | Anderson et al. |
| 7,267,645 B2 | 9/2007 | Anderson et al. |
| 7,270,651 B2 | 9/2007 | Adams et al. |
| 7,273,448 B2 | 9/2007 | Arnal et al. |
| 7,291,104 B2 | 11/2007 | Neisz et al. |
| 7,335,189 B2 | 2/2008 | Harvie |
| 7,384,390 B2 | 6/2008 | Furness et al. |
| 7,422,105 B2 | 9/2008 | Loyd et al. |
| 7,422,557 B2 | 9/2008 | Arnal et al. |
| 7,431,690 B2 | 10/2008 | Merade et al. |
| 7,473,261 B2 | 1/2009 | Rennich |
| 7,523,825 B2 | 4/2009 | Velazquez et al. |
| 7,553,159 B1 | 6/2009 | Arnal et al. |
| 7,553,300 B2 | 6/2009 | Elfstrom et al. |
| 7,559,885 B2 | 7/2009 | Merade et al. |
| 7,608,036 B2 | 10/2009 | Raz et al. |
| 7,637,860 B2 | 12/2009 | MacLean |
| 7,642,395 B2 | 1/2010 | Schroeder et al. |
| 7,654,950 B2 | 2/2010 | Yachia et al. |
| 7,658,195 B2 | 2/2010 | Dennis |
| 7,658,730 B2 | 2/2010 | Conley |
| 7,678,093 B2 * | 3/2010 | Nordness et al. ......... 604/385.08 |
| 7,686,760 B2 | 3/2010 | Anderson et al. |
| 7,687,680 B2 | 3/2010 | Fell et al. |
| 7,713,188 B2 | 5/2010 | Bouffier |
| 7,753,839 B2 | 7/2010 | Siegel et al. |
| 7,762,942 B2 | 7/2010 | Neisz et al. |
| 7,780,006 B2 | 8/2010 | Clark, Jr. et al. |
| 7,993,318 B2 * | 8/2011 | Olsson et al. ............ 604/385.13 |
| 8,052,663 B2 * | 11/2011 | Harsjo ..................... 604/349 |
| 2001/0023356 A1 | 9/2001 | Raz et al. |
| 2001/0031933 A1 | 10/2001 | Cannon |
| 2002/0007160 A1 | 1/2002 | Miskie |
| 2002/0017303 A1 | 2/2002 | Single et al. |
| 2002/0025334 A1 | 2/2002 | Smith |
| 2002/0026163 A1 | 2/2002 | Grundke |
| 2002/0040213 A1 | 4/2002 | Tweddell, III et al. |
| 2002/0055730 A1 | 5/2002 | Yachia et al. |
| 2002/0062113 A1 * | 5/2002 | Thomas et al. ............ 604/378 |
| 2002/0082551 A1 | 6/2002 | Yachia et al. |
| 2002/0087130 A1 | 7/2002 | Guldfeldt et al. |
| 2002/0099258 A1 | 7/2002 | Staskin et al. |
| 2002/0099259 A1 | 7/2002 | Anderson et al. |
| 2002/0107430 A1 | 8/2002 | Neisz et al. |
| 2002/0111640 A1 | 8/2002 | Krause et al. |
| 2002/0120219 A1 | 8/2002 | Hovland et al. |
| 2002/0147382 A1 | 10/2002 | Neisz et al. |
| 2002/0153013 A1 | 10/2002 | Single et al. |
| 2002/0161382 A1 | 10/2002 | Neisz et al. |
| 2002/0165427 A1 | 11/2002 | Yachia et al. |
| 2002/0177825 A1 | 11/2002 | Scovel |
| 2002/0185138 A1 | 12/2002 | Single et al. |
| 2002/0188265 A1 | 12/2002 | Law |
| 2002/0193763 A1 | 12/2002 | Kulikov |
| 2003/0004478 A1 | 1/2003 | Mattsson |
| 2003/0014031 A1 | 1/2003 | Tanzer |
| 2003/0023136 A1 | 1/2003 | Raz et al. |
| 2003/0023222 A1 | 1/2003 | Chen |
| 2003/0028161 A1 | 2/2003 | Carballo |
| 2003/0045774 A1 | 3/2003 | Staskin et al. |
| 2003/0050530 A1 | 3/2003 | Neisz et al. |
| 2003/0130670 A1 | 7/2003 | Anderson et al. |
| 2003/0135225 A1 | 7/2003 | Harari et al. |
| 2003/0171644 A1 | 9/2003 | Anderson et al. |
| 2003/0176875 A1 | 9/2003 | Anderson et al. |
| 2003/0204176 A1 | 10/2003 | Besoyan |
| 2003/0212305 A1 | 11/2003 | Anderson et al. |
| 2003/0216814 A1 | 11/2003 | Siegel et al. |
| 2004/0015048 A1 | 1/2004 | Neisz et al. |
| 2004/0024341 A1 * | 2/2004 | Jacobs .......................... 602/72 |
| 2004/0049166 A1 | 3/2004 | Chen et al. |
| 2004/0059308 A1 | 3/2004 | Odderson |
| 2004/0067967 A1 | 4/2004 | Barden et al. |
| 2004/0068159 A1 | 4/2004 | Neisz et al. |
| 2004/0073180 A1 | 4/2004 | Strannemalm |
| 2004/0074503 A1 | 4/2004 | Claren et al. |
| 2004/0087921 A1 | 5/2004 | Guldfeldt et al. |
| 2004/0092902 A1 * | 5/2004 | Hoffman et al. ........ 604/385.101 |
| 2004/0102753 A1 | 5/2004 | Butler |
| 2004/0106845 A1 | 6/2004 | Anderson et al. |
| 2004/0106909 A1 | 6/2004 | Browning |
| 2004/0111073 A1 | 6/2004 | Hermansson et al. |
| 2004/0112392 A1 | 6/2004 | Parkes |
| 2004/0116773 A1 | 6/2004 | Furness et al. |
| 2004/0127864 A1 * | 7/2004 | Sugito ......................... 604/346 |
| 2004/0129277 A1 | 7/2004 | Parkes |
| 2004/0140048 A1 | 7/2004 | Lindsay et al. |
| 2004/0143343 A1 | 7/2004 | Grocela |
| 2004/0162460 A1 | 8/2004 | Shah et al. |
| 2004/0193215 A1 | 9/2004 | Harari et al. |
| 2004/0215054 A1 | 10/2004 | Siegel et al. |
| 2004/0230180 A1 | 11/2004 | Goulter |
| 2004/0242956 A1 | 12/2004 | Scorvo |
| 2004/0253894 A1 | 12/2004 | Fell et al. |
| 2004/0254548 A1 | 12/2004 | Sachse |
| 2005/0004424 A1 | 1/2005 | Raz et al. |
| 2005/0004426 A1 | 1/2005 | Raz et al. |
| 2005/0027160 A1 | 2/2005 | Siegel et al. |
| 2005/0055104 A1 | 3/2005 | Arnal et al. |
| 2005/0085835 A1 | 4/2005 | Rennich |
| 2005/0090790 A1 | 4/2005 | Veith |
| 2005/0101923 A1 | 5/2005 | Elson et al. |
| 2005/0101924 A1 | 5/2005 | Elson et al. |
| 2005/0119710 A1 | 6/2005 | Furness et al. |
| 2005/0131361 A1 | 6/2005 | Miskie |
| 2005/0143618 A1 | 6/2005 | Anderson et al. |
| 2005/0145523 A1 | 7/2005 | Zander et al. |
| 2005/0148979 A1 | 7/2005 | Palma et al. |
| 2005/0154365 A1 | 7/2005 | Zander et al. |
| 2005/0172963 A1 | 8/2005 | Hishida |
| 2005/0192551 A1 | 9/2005 | Reddy |
| 2005/0240076 A1 | 10/2005 | Neisz et al. |
| 2005/0267426 A1 | 12/2005 | Shedrick |
| 2005/0267436 A1 | 12/2005 | Mishima |
| 2005/0278839 A1 * | 12/2005 | Atwater et al. ................... 2/466 |
| 2005/0283127 A1 | 12/2005 | Miskie |
| 2006/0009793 A1 | 1/2006 | Rennich |
| 2006/0015001 A1 | 1/2006 | Staskin et al. |
| 2006/0015082 A1 | 1/2006 | Pearson et al. |
| 2006/0025739 A1 | 2/2006 | DiPalma et al. |
| 2006/0063968 A1 | 3/2006 | Anderson et al. |
| 2006/0069301 A1 | 3/2006 | Neisz et al. |

| | | | |
|---|---|---|---|
| 2006/0071061 A1 | 4/2006 | Velazquez et al. | |
| 2006/0081265 A1 | 4/2006 | Warden | |
| 2006/0100596 A1 | 5/2006 | Miskie | |
| 2006/0122568 A1 | 6/2006 | Elson et al. | |
| 2006/0124494 A1 | 6/2006 | Clark et al. | |
| 2006/0135926 A1 | 6/2006 | Dick et al. | |
| 2006/0135927 A1 | 6/2006 | Zander et al. | |
| 2006/0140924 A1 | 6/2006 | Schroeder et al. | |
| 2006/0142720 A1 | 6/2006 | Zander et al. | |
| 2006/0149196 A1 | 7/2006 | Bjornberg et al. | |
| 2006/0155163 A1 | 7/2006 | Yachia et al. | |
| 2006/0178649 A1 | 8/2006 | Ma | |
| 2006/0183966 A1 | 8/2006 | Neisz et al. | |
| 2006/0195007 A1 | 8/2006 | Anderson et al. | |
| 2006/0195011 A1 | 8/2006 | Arnal et al. | |
| 2006/0206085 A1 | 9/2006 | Gegelys et al. | |
| 2006/0229576 A1 | 10/2006 | Conway et al. | |
| 2006/0235262 A1 | 10/2006 | Arnal et al. | |
| 2006/0247490 A1 | 11/2006 | Merade et al. | |
| 2006/0252980 A1 | 11/2006 | Arnal et al. | |
| 2006/0276764 A1 | 12/2006 | Warne | |
| 2006/0282055 A1 | 12/2006 | Shiomi | |
| 2006/0287571 A1 | 12/2006 | Gozzi et al. | |
| 2007/0005076 A1 | 1/2007 | Arnal | |
| 2007/0015952 A1 | 1/2007 | Chang et al. | |
| 2007/0038193 A1 | 2/2007 | Miskie | |
| 2007/0043329 A1 | 2/2007 | Evans | |
| 2007/0045144 A1 | 3/2007 | Wheeler et al. | |
| 2007/0045324 A1 | 3/2007 | Mitchell et al. | |
| 2007/0045325 A1 | 3/2007 | Jackson et al. | |
| 2007/0045326 A1 | 3/2007 | Tramontina et al. | |
| 2007/0045483 A1 | 3/2007 | Johnson et al. | |
| 2007/0049791 A1 | 3/2007 | Merade et al. | |
| 2007/0073252 A1 | 3/2007 | Forgrave | |
| 2007/0083175 A1 | 4/2007 | Van Himbergen et al. | |
| 2007/0090009 A1 | 4/2007 | Clare et al. | |
| 2007/0106240 A1* | 5/2007 | Nakajima et al. | 604/385.19 |
| 2007/0117880 A1 | 5/2007 | Elson et al. | |
| 2007/0123746 A1 | 5/2007 | MacLean | |
| 2007/0151885 A1 | 7/2007 | Loyd et al. | |
| 2007/0151887 A1 | 7/2007 | Clark et al. | |
| 2007/0161850 A1 | 7/2007 | Harari et al. | |
| 2007/0162120 A1 | 7/2007 | Bouffier | |
| 2007/0175487 A1 | 8/2007 | Eid | |
| 2007/0197983 A1 | 8/2007 | Giles Finn | |
| 2007/0197985 A1 | 8/2007 | Miskie | |
| 2007/0219606 A1 | 9/2007 | Moreci et al. | |
| 2007/0225546 A1 | 9/2007 | Anderson et al. | |
| 2007/0255244 A1 | 11/2007 | Olsson et al. | |
| 2007/0287973 A1 | 12/2007 | Cohen et al. | |
| 2008/0009665 A1 | 1/2008 | Merade et al. | |
| 2008/0021263 A1 | 1/2008 | Escude et al. | |
| 2008/0021264 A1 | 1/2008 | Neisz et al. | |
| 2008/0077104 A1 | 3/2008 | Baer et al. | |
| 2008/0082070 A1 | 4/2008 | Fell et al. | |
| 2008/0082072 A1 | 4/2008 | Helmfridsson et al. | |
| 2008/0121241 A1 | 5/2008 | Dennis | |
| 2008/0140035 A1 | 6/2008 | Gadzik et al. | |
| 2008/0146868 A1 | 6/2008 | Henri Robert et al. | |
| 2008/0177132 A1 | 7/2008 | Alinsod et al. | |
| 2008/0195172 A1 | 8/2008 | Furness et al. | |
| 2008/0207989 A1 | 8/2008 | Kaleta et al. | |
| 2008/0234642 A1 | 9/2008 | Patterson et al. | |
| 2008/0243097 A1 | 10/2008 | Goss | |
| 2008/0269547 A1 | 10/2008 | Hortenstine | |
| 2008/0287904 A1 | 11/2008 | Drevik et al. | |
| 2009/0023978 A1 | 1/2009 | Arnal et al. | |
| 2009/0090364 A1 | 4/2009 | Daugaard et al. | |
| 2009/0112052 A1 | 4/2009 | Lund et al. | |
| 2009/0143637 A1 | 6/2009 | Raz et al. | |
| 2009/0154842 A1 | 6/2009 | Johnson et al. | |
| 2009/0158505 A1 | 6/2009 | Fleming et al. | |
| 2009/0182190 A1 | 7/2009 | Dann | |
| 2009/0188824 A1 | 7/2009 | Velazquez et al. | |
| 2009/0221867 A1 | 9/2009 | Ogdahl et al. | |
| 2009/0247816 A1 | 10/2009 | Merade et al. | |
| 2009/0264698 A1 | 10/2009 | Arnal et al. | |
| 2009/0264843 A1* | 10/2009 | Reddy | 604/361 |
| 2009/0281510 A1 | 11/2009 | Fisher | |
| 2009/0287229 A1 | 11/2009 | Ogdahl | |
| 2010/0016821 A1 | 1/2010 | Bjerregaard | |
| 2010/0030016 A1 | 2/2010 | Knoll | |
| 2010/0056857 A1 | 3/2010 | Nordmeyer | |
| 2010/0094079 A1 | 4/2010 | Inman et al. | |
| 2010/0094237 A1 | 4/2010 | Margolis et al. | |
| 2010/0114510 A1 | 5/2010 | Vaingast | |
| 2010/0130814 A1 | 5/2010 | Dubernard | |
| 2010/0168505 A1 | 7/2010 | Inman et al. | |
| 2010/0179376 A1 | 7/2010 | Kassab et al. | |
| 2010/0191039 A1 | 7/2010 | Anderson et al. | |
| 2010/0197998 A1 | 8/2010 | Comiter et al. | |
| 2010/0197999 A1 | 8/2010 | Deegan et al. | |
| 2010/0228217 A1 | 9/2010 | Harsjo | |

FOREIGN PATENT DOCUMENTS

| | | |
|---|---|---|
| EP | 57057 B1 | 8/1982 |
| EP | 68712 A1 | 1/1983 |
| EP | 94614 A1 | 11/1983 |
| EP | 119265 B1 | 9/1984 |
| EP | 122344 A1 | 10/1984 |
| EP | 122344 B1 | 10/1984 |
| EP | 130061 A1 | 1/1985 |
| EP | 130061 B1 | 1/1985 |
| EP | 153811 B1 | 9/1985 |
| EP | 161047 A1 | 11/1985 |
| EP | 161047 B1 | 11/1985 |
| EP | 174756 A2 | 3/1986 |
| EP | 174756 B1 | 3/1986 |
| EP | 186209 A2 | 7/1986 |
| EP | 236458 B1 | 9/1987 |
| EP | 292162 A1 | 11/1988 |
| EP | 297769 A1 | 1/1989 |
| EP | 302523 A2 | 2/1989 |
| EP | 314258 A2 | 5/1989 |
| EP | 315305 A2 | 5/1989 |
| EP | 315305 B1 | 5/1989 |
| EP | 403101 A1 | 12/1990 |
| EP | 409455 A1 | 1/1991 |
| EP | 592001 A1 | 4/1994 |
| EP | 592001 B1 | 4/1994 |
| EP | 650710 A1 | 5/1995 |
| EP | 650710 B1 | 5/1995 |
| EP | 666070 A1 | 8/1995 |
| EP | 666070 B1 | 8/1995 |
| EP | 801549 B1 | 10/1997 |
| EP | 850603 B1 | 7/1998 |
| EP | 855873 A4 | 8/1998 |
| EP | 1020195 A1 | 7/2000 |
| EP | 1033955 B1 | 9/2000 |
| EP | 1075245 B1 | 2/2001 |
| EP | 1136051 A1 | 9/2001 |
| EP | 1237522 B1 | 9/2002 |
| EP | 1365713 B1 | 12/2003 |
| EP | 1545404 B1 | 6/2005 |
| EP | 1020195 B1 | 7/2009 |
| GB | 1332447 A | 10/1973 |
| GB | 1521064 A | 8/1978 |
| GB | 2137505 A | 10/1984 |
| GB | 2149412 A | 6/1985 |
| GB | 2168899 A | 7/1986 |
| GB | 2171911 A | 9/1986 |
| GB | 2185401 A | 7/1987 |
| GB | 2191095 A | 12/1987 |
| GB | 2195541 A | 4/1988 |
| GB | 2206050 A | 12/1988 |
| GB | 2235383 A | 3/1991 |
| GB | 2252247 A | 8/1992 |
| GB | 2278279 A | 11/1994 |
| GB | 2283177 A | 5/1995 |
| GB | 2286339 A | 8/1995 |
| GB | 2290970 A | 1/1996 |
| GB | 2290972 A | 1/1996 |
| GB | 2293107 A | 3/1996 |
| GB | 2324706 A | 11/1998 |
| GB | 2348609 B | 5/2003 |
| GB | 2375321 B | 1/2004 |
| GB | 2423475 A | 8/2006 |
| GB | 2462267 A | 2/2010 |

| | | |
|---|---|---|
| WO | 84/01098 | 3/1984 |
| WO | 86/00816 | 2/1986 |
| WO | 87/07136 | 12/1987 |
| WO | 88/02624 | 4/1988 |
| WO | 89/00037 | 1/1989 |
| WO | 91/07155 | 5/1991 |
| WO | 91/07156 | 5/1991 |
| WO | 92/00048 | 1/1992 |
| WO | WO 9215269 * | 9/1992 |
| WO | 95/01143 | 1/1995 |
| WO | 95/01144 | 1/1995 |
| WO | 95/15736 | 6/1995 |
| WO | 95/34253 | 12/1995 |
| WO | 96/05786 | 2/1996 |
| WO | 96/05789 | 2/1996 |
| WO | 96/20665 | 7/1996 |
| WO | 96/20753 | 7/1996 |
| WO | 97/13480 | 4/1997 |
| WO | 97/14353 | 4/1997 |
| WO | 98/00191 | 1/1998 |
| WO | 98/14146 | 4/1998 |
| WO | 98/29061 | 7/1998 |
| WO | 98/29073 | 7/1998 |
| WO | 98/37862 | 9/1998 |
| WO | 99/06077 | 2/1999 |
| WO | 99/22679 | 5/1999 |
| WO | 99/26573 | 6/1999 |
| WO | 99/26574 | 6/1999 |
| WO | 99/26575 | 6/1999 |
| WO | 99/43276 | 9/1999 |
| WO | 00/13622 | 3/2000 |
| WO | 00/13623 | 3/2000 |
| WO | 00/13640 | 3/2000 |
| WO | 00/33773 | 6/2000 |
| WO | 00/40158 | 7/2000 |
| WO | 00/54701 | 9/2000 |
| WO | 00/54702 | 9/2000 |
| WO | 00/59427 | 10/2000 |
| WO | 01/00128 | 1/2001 |
| WO | 01/10357 | 2/2001 |
| WO | 01/26592 | 4/2001 |
| WO | 01/26595 | 4/2001 |
| WO | 01/62192 | 8/2001 |
| WO | 01/80800 | 11/2001 |
| WO | 01/91677 | 12/2001 |
| WO | 01/95829 | 12/2001 |
| WO | 02/17929 | 3/2002 |
| WO | 02/38088 | 5/2002 |
| WO | 02/43635 | 6/2002 |
| WO | 02/45640 | 6/2002 |
| WO | 02/49562 | 6/2002 |
| WO | 02/053070 | 7/2002 |
| WO | 02/058563 | 8/2002 |
| WO | 02/058564 | 8/2002 |
| WO | 02/058565 | 8/2002 |
| WO | 02/062237 | 8/2002 |
| WO | 02/065959 | 8/2002 |
| WO | 02/065975 | 8/2002 |
| WO | 02/078571 | 10/2002 |
| WO | 03/005947 | 1/2003 |
| WO | 03/068077 | 8/2003 |
| WO | 03/071995 | 9/2003 |
| WO | 03/075792 | 9/2003 |
| WO | 03/094784 | 11/2003 |
| WO | 03/096930 | 11/2003 |
| WO | 2004/004619 | 1/2004 |
| WO | 2004/017862 | 3/2004 |
| WO | 2004/019850 | 3/2004 |
| WO | 2004/026166 | 4/2004 |
| WO | 2004/026194 | 4/2004 |
| WO | 2004/026195 | 4/2004 |
| WO | 2004/041124 | 5/2004 |
| WO | 2004/047696 | 6/2004 |
| WO | 2004/066875 | 8/2004 |
| WO | 2004/071361 | 8/2004 |
| WO | 2004/096087 | 11/2004 |
| WO | 2005/004934 | 1/2005 |
| WO | 2005/044169 | 5/2005 |
| WO | 2005/065605 | 7/2005 |
| WO | 2005/065616 | 7/2005 |
| WO | 2005/092266 | 10/2005 |
| WO | 2005/094252 | 10/2005 |
| WO | 2005/099645 | 10/2005 |
| WO | 2006/044853 | 4/2006 |
| WO | 2006/062567 | 6/2006 |
| WO | 2006/068673 | 6/2006 |
| WO | 2006/071146 | 7/2006 |
| WO | 2006/071335 | 7/2006 |
| WO | 2006/071424 | 7/2006 |
| WO | 2006/084165 | 8/2006 |
| WO | 2006/084167 | 8/2006 |
| WO | 2006/086289 | 8/2006 |
| WO | 2006/110695 | 10/2006 |
| WO | 2006/119273 | 11/2006 |
| WO | 2006/123973 | 11/2006 |
| WO | 2007/002012 | 1/2007 |
| WO | 2007/002056 | 1/2007 |
| WO | 2007/002071 | 1/2007 |
| WO | 2007/008275 | 1/2007 |
| WO | 2007/027261 | 3/2007 |
| WO | 2007/027264 | 3/2007 |
| WO | 2007/027372 | 3/2007 |
| WO | 2007/027592 | 3/2007 |
| WO | 2007/027897 | 3/2007 |
| WO | 2007/027900 | 3/2007 |
| WO | 2007/038988 | 4/2007 |
| WO | 2007/046969 | 4/2007 |
| WO | 2007/046970 | 4/2007 |
| WO | 2007/059306 | 5/2007 |
| WO | 2007/059368 | 5/2007 |
| WO | 2007/061341 | 5/2007 |
| WO | 2007/074144 | 7/2007 |
| WO | 2007/078392 | 7/2007 |
| WO | 2007/078535 | 7/2007 |
| WO | 2007/097994 | 8/2007 |
| WO | 2007/106520 | 9/2007 |
| WO | 2007/122505 | 11/2007 |
| WO | 2007/144791 | 12/2007 |
| WO | 2007/149348 | 12/2007 |
| WO | 2008/033950 | 3/2008 |
| WO | 2008/035241 | 3/2008 |
| WO | 2008/048971 | 4/2008 |
| WO | 2008/058163 | 5/2008 |
| WO | 2008/088911 | 7/2008 |
| WO | 2008/106137 | 9/2008 |
| WO | 2008/118389 | 10/2008 |
| WO | 2008/121109 | 10/2008 |
| WO | 2008/121110 | 10/2008 |
| WO | 2008/150878 | 12/2008 |
| WO | 2009/008790 | 1/2009 |
| WO | 2009/009832 | 1/2009 |
| WO | 2009/077903 | 6/2009 |
| WO | 2010/017291 | 2/2010 |
| WO | 2010/025444 | 3/2010 |
| WO | 2010/039068 | 4/2010 |
| WO | 2010/039259 | 4/2010 |
| WO | 2010/066932 | 6/2010 |
| WO | 2010/071517 | 6/2010 |
| WO | 2010/075292 | 7/2010 |

OTHER PUBLICATIONS

Flickr (http://farm3.static.flickr.com/2104/2321984979_cb638f80d1.jpg), Cup size comparison, last visited Jul. 29, 2009.
Protective cup (http://en.wikipedia.org/wiki/Protective_cup#protective-cup), last visited Nov. 19, 2009.
Always ultra thin pads packaging listing the following U.S. Patents: 4950264, 5009653, 5267992, 5354400, 5389094, 5413568, 5462166, 5520875, 5569231, 5620430, 5704930, 5800654 ,6231555, 6601705, 7163528, 7185761, 7241280, 7270651, 7306582, 7311696.
Always pad.
Respirator, 3M 8246, exterior view.
Respirator, 3M 8246, interior view.
ProCup, XO Athletic, interior view.
ProCup, XO Athletic, exterior view.
Washable Briefs packaging, P&S Healthcare Ltd., pshealthcare.co.uk.

Disposable Protective Underwear packaging, Kroger Co Cincinnati, OH 45202, showing pat. pending.
Disposable Protective Underwear, Kroger Co., interior view.
Drip Collector packaging, side one, Conveen by Coloplast, 1955 W. Oak Cir., Marietta, Ca 30062.
Drip Collector packaging, side two, Conveen by Coloplast, 1955 W. Oak Cir., Marietta, Ga 30062.
Drip Collector, Conveen by Coloplast.

Kotex Ultra Thin with wings packaging, side one, www.kotex.com, Kimberly-Clark, Box 2020, Neenah, WI 54957-2020.
Kotex Ultra Thin with wings packaging, side two, www.kotex.com, Kimberly-Clark, Box 2020, Neenah, WI 54957-2020.
Kotex Ultra Thin with wings.
Washable Briefs, P&S Healthcare Ltd., pshealthcare.co.uk.
Washable Boxers, P&S Healthcare Ltd., pshealthcare.co.uk.

* cited by examiner

MALE URINARY INCONTINENCE DEVICE

TECHNICAL FIELD

This description relates to absorbent devices, particularly to devices for absorbing urine discharge resulting from male urinary incontinence.

BACKGROUND

Male urinary incontinence may be caused by a variety of factors. It can occur, in varying degrees, in infant males not yet toilet trained, young boys suffering from nocturnal enuresis (bed wetting), men who have undergone a prostatectomy (surgical removal of the prostate) or other urinary tract surgeries, such as a cystectomy (surgical removal of the bladder), in diabetics with nerve damage, and in men who have had a stroke or spinal cord injury or who suffer from Parkinson's disease or multiple sclerosis. Aging is also a leading cause of male incontinence. Other causes include loss of control from such actions as coughing, sneezing, and lifting, and an abnormal and overwhelming urge to urinate caused, for example, by various bladder conditions such as exposure to radiation therapy. Finally, men who are handicapped or otherwise medically compromised may have problems with incontinence. Urinary incontinence can be more than an inconvenience and an embarrassment to men, it can cause discomfort from being in wet or damp clothing as well as genital itching or a rash or infection caused by contact with discharged urine.

Conventional absorbent devices to help manage male urinary incontinence include those which are positioned beneath undergarments and next to the genitals. Discharged urine is retained within an absorbent layer while a moisture barrier layer is interposed between the retained urine and the undergarments and other clothing. In this way, discharged urine is retained and not allowed to leak onto, or otherwise soil, clothing. In addition, the anxiety and potential embarrassment of being seen with soiled clothing is avoided. The used absorbent device is then later disposed of at an appropriate time. Such devices include diapers, which enclose the genitals, perineum, and buttocks, and pads, which enclose only the genital region.

While such absorbent devices may be effective in absorbing urine and preventing soiled clothing, a bulky or protruding appearance may call attention to the problem, the genitals may be allowed to come into contact with discharged urine and may become too warm, with resultant discomfort and the chance of rash or infection, and, the device may cause further discomfort by not remaining in place while allowing the wearer to move about freely and engage in normal daily activities.

Thus, there is a need for a male urinary incontinence device that is not only effective, but that fits the male genital anatomy comfortably, allows sufficient freedom of movement to permit normal daily activities, may be worn discretely, and that helps the genitals from becoming too warm and helps prevent the genitals from coming into contact with discharged urine.

SUMMARY

Devices of the present invention help prevent soiling of clothing with discharged urine, provide comfort to the male genitalia, allow sufficient freedom of movement to permit normal daily activities, and help separate the genitalia from discharged urine, thus providing a more natural feel. In one embodiment, a male urinary incontinence device includes a body which has a shell which forms a cavity adapted to hold male genitalia. Disposed within the cavity is an absorbent suitable for absorbing and storing discharged urine. A moisture barrier adjacent the body and placed between the absorbent and the clothing of the wearer to help prevent soiling of the clothing. A liquid-permeable liner is attached to the body so as to provide a gap between the liner and the absorbent. This hammock-like effect creates an air space and holds the male genitalia away from the discharged urine stored in the absorbent. When necessary, the device is removed and discarded.

In one embodiment, the shell is formed from a flexible, semi-rigid shell. The body may further include a flexible, non-rigid crest extending from the shell at the top of the device and may further include a flexible, non-rigid tongue ex-tending from the shell at the bottom of the device. In a further embodiment, the crest extends between about 15 percent and about 20 percent of the length of the body. In a further embodiment, the crest extends between about 2-5 cm from the shell. In a further embodiment, the tongue extends between about 25 percent and about 30 percent of the length of the body. In a further embodiment, the tongue extends from the shell about 4 cm. In a further embodiment, the overall length of the body is between about 16 cm and about 20 cm. In a further embodiment, the tongue forms an angle of between about 30 degrees and about 50 degrees.

In one embodiment, the device forms a length external angle of between about 70 degrees and about 100 degrees. In a further embodiment, the device forms a width internal angle of between about 85 degrees and about 105 degrees.

Additional objects, features, and advantages of the invention will become apparent to those skilled in the relevant art upon consideration of the following detailed description of preferred embodiments exemplifying the best mode of carrying out the invention as presently perceived.

BRIEF DESCRIPTION OF THE SEVERAL VIEWS OF THE DRAWING

The accompanying drawings, which are incorporated in, and constitute a part of, this specification, illustrate several embodiments consistent with the invention and, together with the description, serve to explain the principles of the invention. For purposes of illustration, drawings may not be to scale.

DETAILED DESCRIPTION

Figures 1, 2:
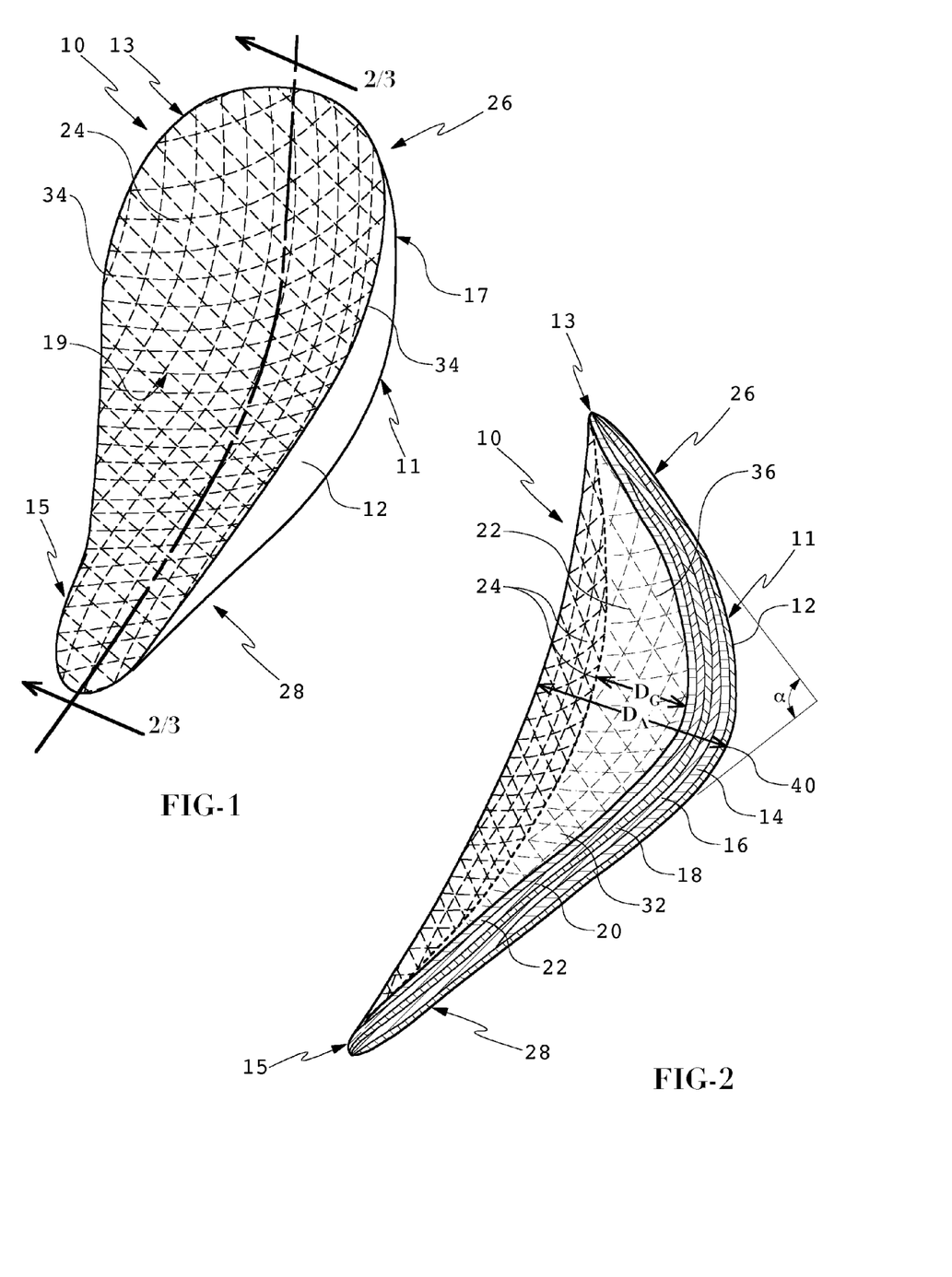
FIG. 1 is a perspective view of a male urinary incontinence device according to an embodiment of the present invention.
FIG. 2 is a cross-sectional view taken generally along the plane of the line 2-2 in FIG. 1 and illustrating an embodiment of the present invention.

In one embodiment, shown in FIG. 1, a male incontinence device 10 includes a body 11 and a first liquid-permeable liner 24. The device 10 has a top 13 which, when worn, points generally toward the navel of the wearer, and a bottom 15 which, when worn, points generally toward the perineum of the wearer. The device 10 further has an external side 17 which, when worn, faces away from the wearer, and an interior side 19 which, when worn, faces the wearer and, particularly, the genitalia 38 of the wearer. See, FIG. 5.

Figure 5:
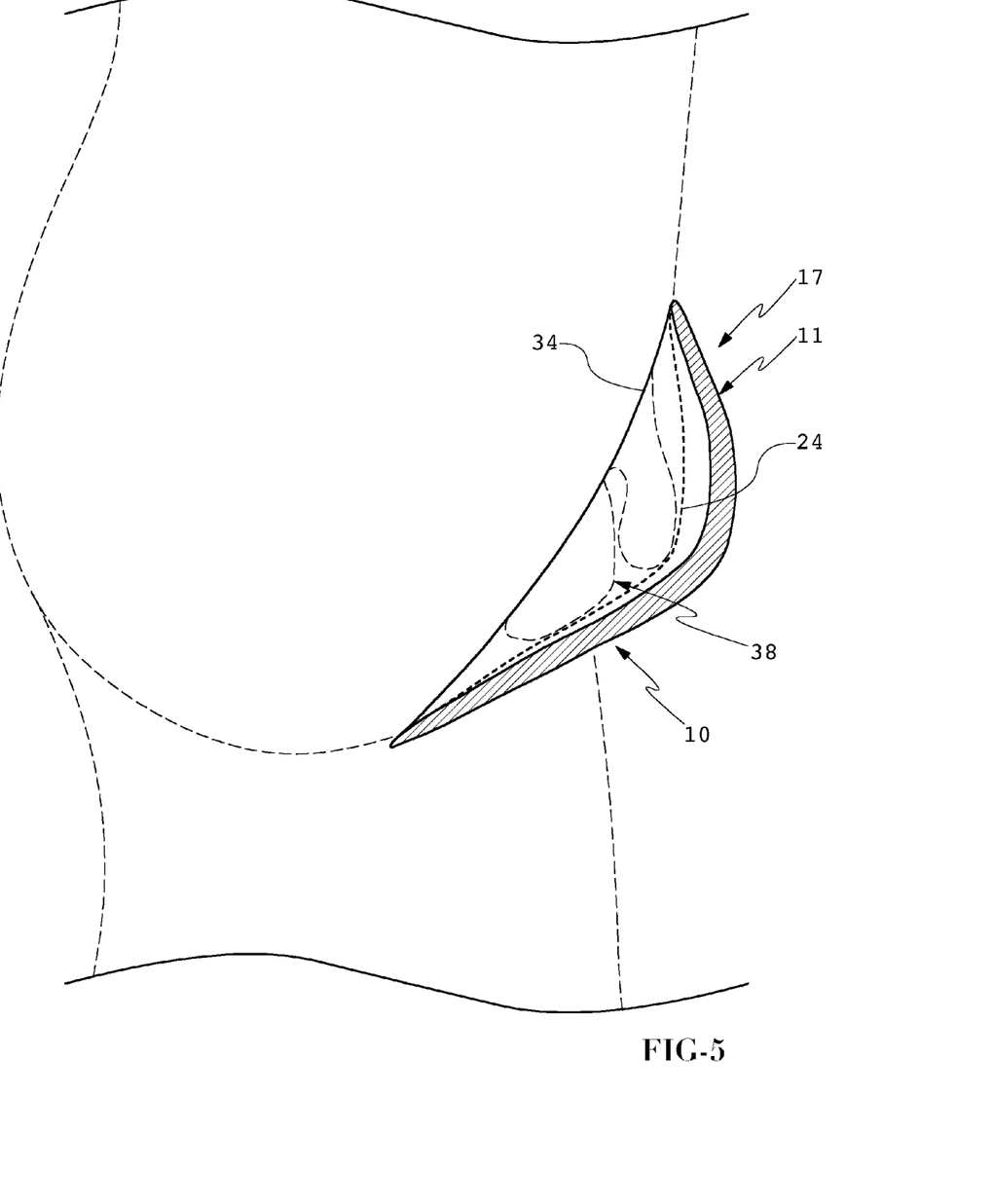
FIG. 5 is a cross-sectional side view of an embodiment of the present invention illustrated in FIGS. 1 and 2 and including a representation of the male anatomy while the device is in use.
Figure 7:
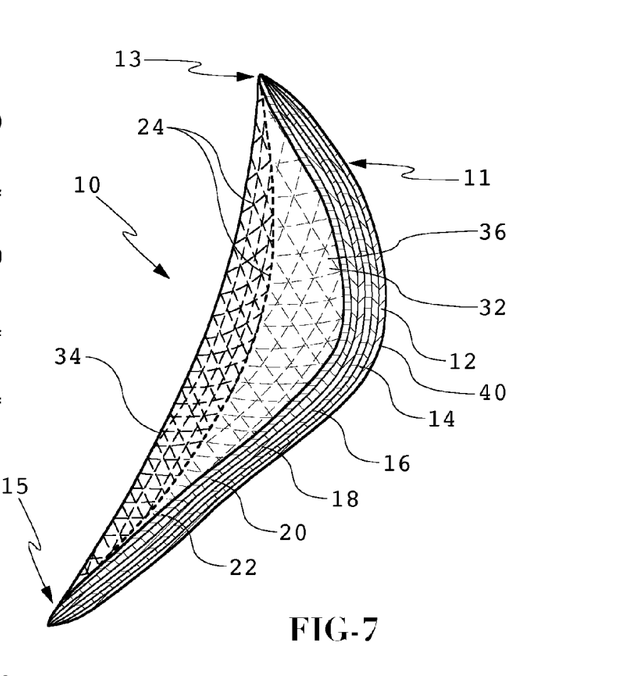
FIG. 7 is a cross-sectional view taken generally along the plane of the line 7-7 in FIG. 6 and illustrating an embodiment of the present invention.

The body 11 forms a cavity 36 (see, also, FIGS. 2, 3, 5, and 7) adapted to hold human male genitalia 38 and includes a shell 14 and may further include a crest 26 at the top 13 and may further include a tongue 28 at the bottom 15. Note that the neither the crest 26 nor the tongue 28 are shown in FIGS. 5 and 7. Especially when the shell 14 is comprised of flexible, semi-rigid material as described below, the device 10 is easily moved to the side while being worn to facilitate normal male urination. The device 10 also includes at least one moisture barrier 12, 16 adapted to prevent moisture, and specifically urine, from wetting the clothes of the wearer.

Figures 3, 4:
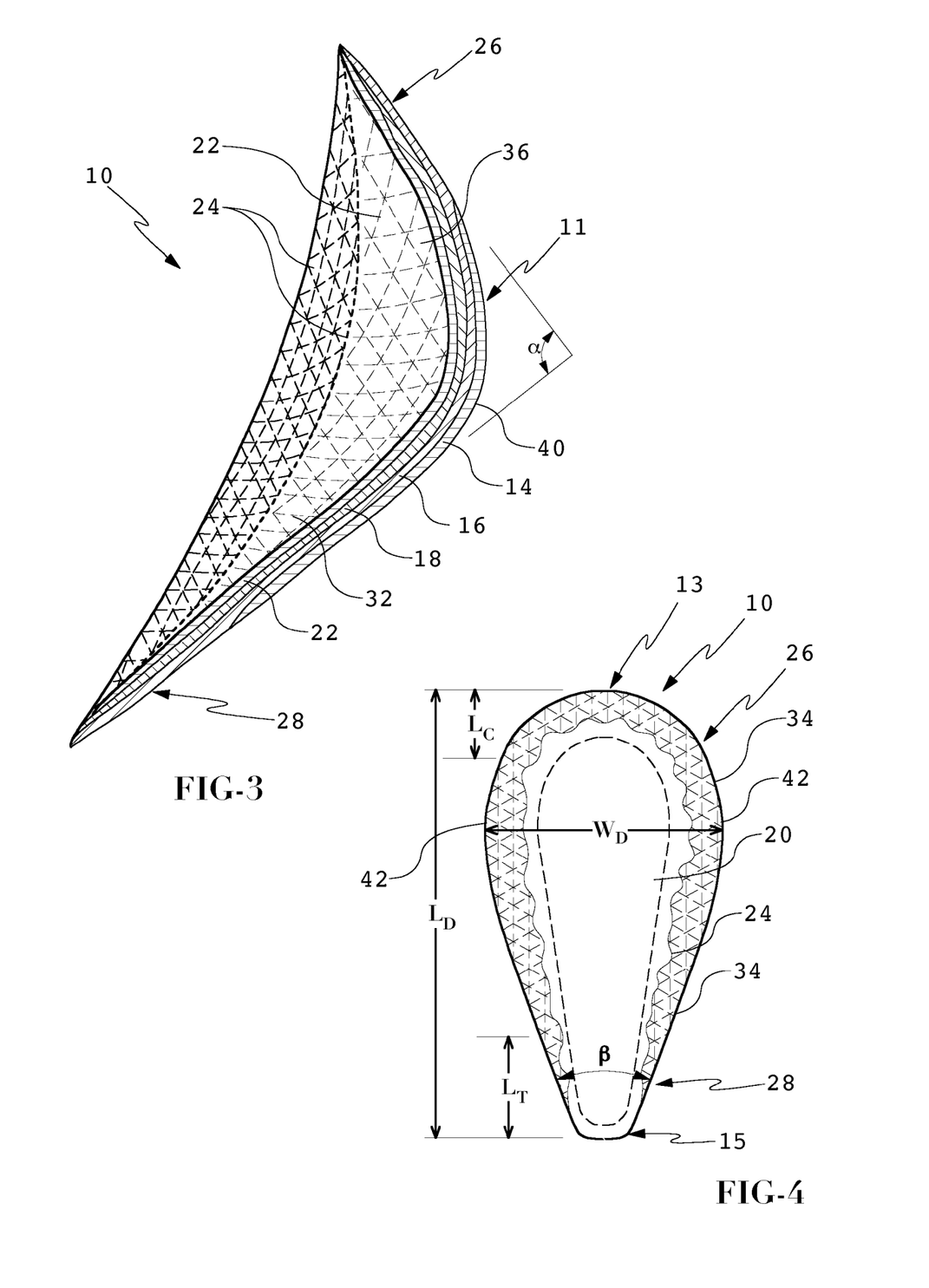
FIG. 3 is a cross-sectional view taken generally along the plane of the line 3-3 in FIG. 1 and illustrating an embodiment of the present invention.
FIG. 4 is a view of an interior side of a male urinary incontinence device according to an embodiment of the present invention.

As best seen in FIGS. 2, 3, and 7, but also in FIG. 5, the first liquid-permeable liner 24 cooperates with the body 11, and particularly the shell 14 to create a gap $D_G$ and a chamber 32. This effect is aided by securing the first liquid-permeable liner 24, having an area sufficient to prevent its total collapse into the body 11. Thus, the first liquid-permeable liner 24 is sufficiently suspended to create the gap $D_G$ and the chamber 32 and acts to hold the male genitalia 38 separated from discharged urine stored in one or more absorbent 18, 20. In this configuration, the first liquid-permeable liner 24 also provides needed support to the male genitalia 38. The gap $D_G$ and the chamber 32 also create an opportunity for air to circulate about the genitals 38 for a further drying effect. While the first liquid-permeable liner 24 may be secured about the periphery 34 of the body 11, the first liquid-permeable liner 24 may also be secured inboard of the periphery 34.

Figure 8:
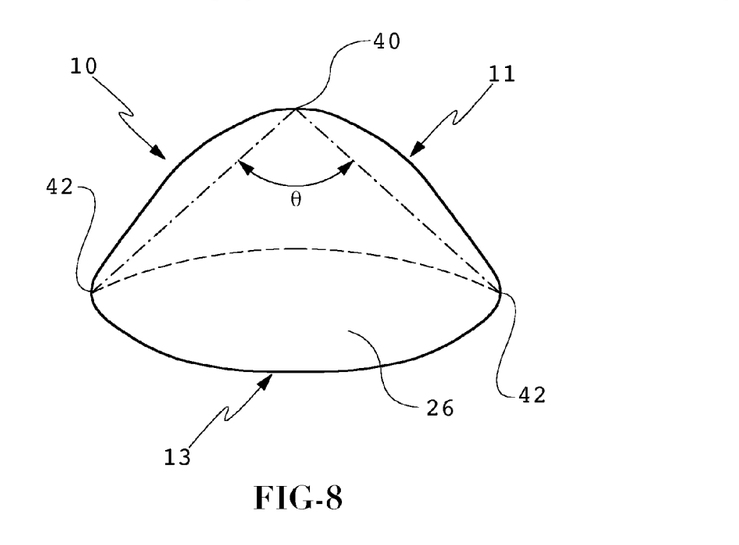
FIG. 8 is a top elevation view of a male urinary incontinence device according to an embodiment of the present invention.

As shown in FIGS. 2 and 3, the device 10 forms a length external angle α and, as shown in FIG. 8, a width internal angle θ. The length external angle α is that angle formed by the intersection of extending a tangent from the top 13 of the device 10 and from the bottom 15 of the device 10. The width internal angle θ is that angle formed between an apex 40 of the external side 17 of the device 10 and edges 42 at the widest point $W_D$ of the device 10.

The length external angle α cooperates with the width external angle θ to accommodate human male genitalia 38 (FIG. 5) and to minimize the characteristic visible "bulge" indicative of men wearing an incontinence device. The length external angle α is between about 70 deg. and about 100 deg. The width internal angle θ is between about 85 deg. and about 105 deg. Proportionally, the width internal angle θ is between about 85 percent and 150 percent of the length external angle α.

As shown in FIGS. 2 and 3, the crest 26 extends from the shell 14 and generally comprises soft, flexible material. The crest 26 forms a comfortable seal at the abdomen of the wearer and can provide additional absorbent protection. Also shown in FIGS. 2 and 3, the tongue 28 extends from the shell 14 and also generally comprises soft, flexible material. The tongue 28 forms a comfortable seal beneath the scrotum and in the perineum. Additionally, the tongue 28 may provide further absorbent protection. The tongue 28 forms an angle β of between about 30 deg. and 50 deg. Both the crest 26 and the tongue 28 provide a comfortable transition from the device 10 to the human body.

In an embodiment, the periphery 34 of the device 10 comprises soft, flexible material for comfort and to help seal the device 10 against the body of the wearer.

As shown in FIGS. 2-4 and in Table 1, below, the device 10 has an overall length $L_D$, a width at the widest part $W_D$, a depth at the apex 40 of $D_A$, a tongue length $L_T$, and a crest length $L_C$. Proportionally, the width $W_D$ is between about 50 percent and about 55 percent of the overall length $L_D$. As will be appreciated by those skilled in the relevant art, the indicated sizes are exemplary only, and smaller, larger, and other intermediate sizes are possible without departing from the spirit of the invention.

Table 1, below, lists representative dimensions for four different sized devices 10. All dimensions are in centimeters (cm).

TABLE 1

| Size | $L_D$ | $W_D$ | $D_A$ | $L_T$ | $L_C$ |
|---|---|---|---|---|---|
| Small (cm) | 16.5 | 9 | 5 | 5 | 3.5 |
| Medium (cm) | 17.5 | 9.5 | 5.5 | 5 | 3.5 |
| Large (cm) | 19 | 9.5 | 6.0 | 5 | 3.5 |
| Extra-Large (cm) | 19.5 | 10 | 6.0 | 5 | 3.5 |

Thus, as Table 1 above shows, the width at the widest point $W_D$ is between about 9 cm and 10 cm, the ratio of the width $W_D$ to overall length $L_D$ ($W_D/L_D$) is between about 45 percent and about 65 percent, the depth of the de-vice at the apex 40 $D_A$ is between about 5 cm and about 6 cm, and the ratio of the depth of the device at the apex 40 $D_A$ to a long axis $L_D$ is between about 25 per-cent and about 40 percent.

In one embodiment, the shell 14 is flexible and semi-rigid and may be molded from a sheet or batt of fibers by placing the fiber sheet of batt between dies and, with the application of heat and pressure, molded into the desired shape. The shell 14 may also be resilient and attempt to return to its original shape when distorting forces are removed. Conventional examples include materials used to make particle masks so manufactured using natural fibers, such as wool and cotton, and synthetic materials, such as nylon, acrylonitrile, polyethylene, polyester, or polypropylene fibers. These fibers are often mixed with chemical resins, such as polyolefinic resins The nominal thickness of the shell 14 is about 2 mm. As will be appreciated by those skilled in the relevant art, various foams and other plastics may also be employed in making the shell 14. The shell 14 is flexible with the pressures due to normal activities while being worn. At the same time, the shell 14 is resistant to flattening out against the genitalia 38. The latter may be aided in part, for example, by molding into the shell 14, elongated ridges to improve shape retention as may be seen in conventional dust masks. An exemplary shell 14 that has been used successfully uses the material of the 8000 series N95 Particle Mask from 3M, St. Paul, Minn. Other, non-limiting, examples include those found in U.S. Pat. Nos. 4,384,577 to Huber et al. and 3,220,409 to Liloia et al.

In a further embodiment, the shell 14 comprises rigid material, plastic, for example. In such an embodiment, the shell 14 can provide further strength to help keep the body 11 from collapsing around the genitalia 38, in the case of penile, testicular, or scrotal surgery, for example.

The first liquid-permeable liner 24 is in contact with the genitalia 38 and serves to allow discharged urine to pass through freely and to keep the genitalia separated from the discharged urine. Preferably, the first liquid-permeable liner 24 is compliant, soft to the touch, and nonirritating. In addition, the first liquid-permeable liner 24 is non-absorbent and preferably formed from rapidly drying material which wicks away moisture quickly. Typically, the liner 24 is a netting material, woven or non-woven, comprised of, for example, polyester, nylon, polypropylene, rayon, or cotton. Other materials include apertured hydrophobic formed film. Exemplary, but non-limiting, formed films include those described in U.S. Pat. Nos. 4,324,246 to Mullane et al. and 4,342,314 to Radel et al. Other, non-limiting, liner materials include that described in U.S. Pat. No. 5,705,249 to Takai et al.

A first absorbent 18 provides collection and storage of discharged urine and is formed of material adapted to absorb and retain human urine. Successful materials include processed wood pulp and super-absorbent polymers found in conventional disposable diapers and feminine hygiene products, such as polyacrylate/polyacrylamide copolymers, ethylene maleic anhydride copolymer, cross-lined carboxy-methyl-cellulose, polyvinyl alcohol copolymers, cross-linked polyethylene oxide, and starch grafted copolymer of polyacrylonitrile.

Turning now to FIGS. 2 and 4, a second absorbent 20 may be included to provide additional absorbent capacity. As shown in FIG. 4, the second absorbent may be limited to a central portion of the device 10 where the majority of the discharged urine would collect. Accordingly, the second absorbent 20 may provide a higher absorbent density so that additional urine can be effectively absorbed and stored.

Exemplary absorbent materials that have been used successfully include those of Always® ultra Thin™ pads (Procter & Gamble, Cincinnati, Ohio). See, for example, U.S. Pat. Nos. 4,950,264 to Osborn, III; 5,520,875 to Wnuk et al.; and 6,601,705 to Molina et al. For other, non-limiting, absorbent materials, see, also, U.S. Pat. Nos. 5,075,344 to Johnson; 3,926,891 to Gross et al.; and 4,293,609 to Erickson.

In a further embodiment, a second liquid-permeable liner 22 may be provided adjacent the absorbent 18, 20. The second liquid-permeable liner 22 may comprise any suitable material for enclosing the absorbent 18, 20. Exemplary materials include apertured hydrophobic formed films discussed above as well as woven and non-woven materials.

Turning again to FIGS. 2, 3, and 7, in a further embodiment, a first moisture barrier 12 is provided on the external side 17 of the device 10. A sheet of thin plastic of the type commonly found in conventional incontinence devices and feminine pads have been used successfully.

In a further embodiment, shown in FIGS. 2 and 3, a second moisture barrier 16 is provided adjacent to the absorbent 18. As with the first moisture barrier 12, the second moisture barrier 16 of the type of thin plastic sheet commonly used in conventional incontinence devices and feminine pads have been used successfully.

Turning now to FIG. 3, an embodiment of a male urinary incontinence device 10 is shown which includes a shell 14, a moisture barrier 16, an absorbent 18, and a second liquid-permeable liner 22. The embodiment shown in FIG. 3 does not include a moisture barrier 12 on the external side of the device 10 and includes just one absorbent 18. The first liquid-permeable liner 24 provides support for the genitalia 38 and helps separate the genitalia 38 from urine stored in the absorbent 18. The shell 14 provides shape for the body 11 and helps to prevent the device 10 from collapsing around the genitalia 38. Finally, the moisture barrier 16, placed between the absorbent 18 and the clothing of the wearer to help protect the clothing from becoming soiled.

Figure 6:
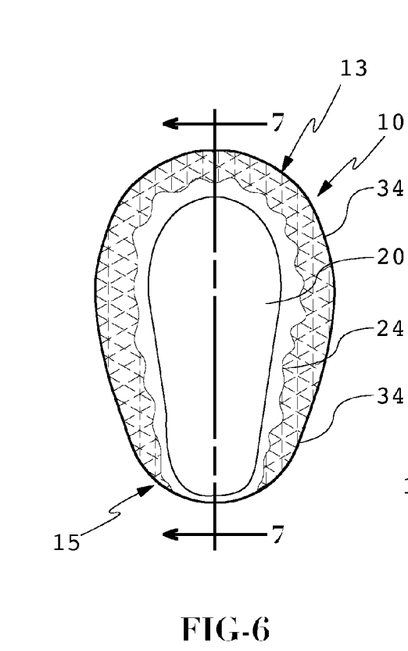
FIG. 6 is a view of an interior side of a male urinary incontinence device according to an embodiment of the present invention.

Turning now to FIGS. 6 and 7, an embodiment of a male urinary incontinence device 10 is shown which includes neither a crest 26 nor a tongue 28.

Experimental Results

In a series of tests, a size small device 10 was used and held in a position similar to that which it would be in when worn and water streamed from a syringe-type delivery apparatus with a slit to mimic the action of urine being excreted from a male penis. In two tests, the absorbent from an Always® Regular feminine hygiene pad absorbed 70 ml before reaching saturation. In one test, the absorbent from an Always® Overnight feminine hygiene pad absorbed 120 ml before reaching saturation.

While certain preferred embodiments of the present invention have been disclosed in detail, it is to be understood that various modifications may be adopted without departing from the spirit of the invention of scope of the following claims.

We claim:

1. A male urinary incontinence device, comprising:
    a body, the body having a periphery, the body further comprising a shell, the shell having a concave inner surface area, the shell concave inner surface area defining a cavity, the cavity adapted to hold male genitalia;
    an absorbent, the absorbent at least partially disposed within the cavity; and
    a first liquid-permeable liner, the liner having:
        a periphery, the liner periphery generally corresponding to the body periphery in length and shape; and
        an area, the liner area being smaller than the concave inner surface area, wherein:
            the liner periphery is attached to the body periphery;
            the liner and the concave inner surface define a chamber; and
            the liner area is sufficiently smaller than the concave inner surface area to, during use, hammock the male genitalia and at least partially maintain the chamber, thereby maintaining a void space between the liner and the absorbent;
            wherein the shell is flexible and semi-rigid.

2. The device of claim 1, wherein the body further comprises a flexible, non-rigid crest, the crest extending from the shell to form a topmost portion of the body beyond the shell.

3. The device of claim 2, wherein the crest extends from the shell about 2-5 cm.

4. The device of claim 2, wherein:
    the body has an overall length along a long axis; and
    the crest extension is between about 15 percent to about 20 percent of the length of the body.

5. The device of claim 1, wherein the body further comprises a flexible, non-rigid tongue, the tongue extending from the shell to form a bottommost portion of the body beyond the shell.

6. The device of claim 5, wherein the tongue extends from the shell about 4 cm.

7. The device of claim 5, wherein:
    the body has an overall length along a long axis; and
    the tongue extension is between about 25 percent to about 30 percent of the length of the body.

8. The device of claim 5, wherein the tongue forms an angle of between about 30 degrees and about 50 degrees.

9. The device of claim 1, wherein the device forms a length external angle of between about 70 degrees and about 100 degrees.

10. The device of claim 1, wherein the device forms a width internal angle of between about 85 degrees and about 105 degrees.

11. The device of claim 1, wherein an overall length along a long axis is between about 16 cm and about 20 cm.

12. The device of claim 1, wherein a width along a short axis at the widest point is between about 9 cm and about 10 cm.

13. The device of claim 1, wherein the ratio of a width along a short axis to a length along a long axis is between about 45 percent and about 65 percent.

14. The device of claim 1, wherein a depth of the device at an apex is between about 5 cm and about 6 cm.

15. The device of claim 1, wherein the ratio of a depth of the device at an apex to a length along a long axis is between about 25 percent and about 40 percent.

16. The device of claim 1, further comprising a first moisture barrier, the first moisture barrier positioned adjacent the body.

17. The device of claim 1, wherein tension of the liner is sufficient to at least partially maintain the chamber during use.

18. The device of claim 1, wherein the cavity is in the shape of a generally hemi-ellipsoidal cup.

19. The device of claim 1, wherein the shell is sufficiently flexible and semi-rigid to deform with the forces due to normal activities while being worn while resistant to flattening out or collapsing against the genitalia.

* * * * *